United States Patent

Mikula-Curtis et al.

[11] Patent Number: 6,135,958
[45] Date of Patent: Oct. 24, 2000

[54] ULTRASOUND IMAGING SYSTEM WITH TOUCH-PAD POINTING DEVICE

[75] Inventors: Anastasia M. Mikula-Curtis, Saratoga; Janice L. Marshall, Sunnyvale; Lawrence M. Bruno, Fremont, all of Calif.

[73] Assignee: Acuson Corporation, Mountain View, Calif.

[21] Appl. No.: 09/130,120

[22] Filed: Aug. 6, 1998

[51] Int. Cl.⁷ ........................................... A61B 8/14
[52] U.S. Cl. .............................................. 600/443; 73/620
[58] Field of Search ............................. 73/618, 619, 620, 73/602; 702/39, 56; 600/437, 443

[56] References Cited

U.S. PATENT DOCUMENTS

| | | |
|---|---|---|
| D. 358,385 | 5/1995 | Franz . |
| D. 359,479 | 6/1995 | Jondrow et al. . |
| D. 360,200 | 7/1995 | Franz . |
| D. 362,431 | 9/1995 | Kaneko et al. . |
| D. 382,550 | 8/1997 | Kaneko et al. . |
| D. 385,542 | 10/1997 | Kaneko et al. . |
| 4,039,940 | 8/1977 | Butler et al. . |
| 4,090,092 | 5/1978 | Serrano . |
| 4,121,204 | 10/1978 | Welch et al. . |
| 4,136,291 | 1/1979 | Waldron . |
| 4,145,748 | 3/1979 | Eichelberger et al. . |
| 4,204,204 | 5/1980 | Pitstick . |
| 4,237,421 | 12/1980 | Waldron . |
| 4,290,052 | 9/1981 | Eichelberger et al. . |
| 4,290,061 | 9/1981 | Serrano . |
| 4,291,303 | 9/1981 | Cutler et al. . |
| 4,368,410 | 1/1983 | Hance et al. . |
| 4,386,347 | 5/1983 | Cutler et al. . |
| 4,394,643 | 7/1983 | Williams . |
| 4,403,291 | 9/1983 | Von Tomkewitsch . |
| 4,464,781 | 8/1984 | Kaneko et al. . |
| 4,561,002 | 12/1985 | Chiu . |
| 4,594,481 | 6/1986 | Wilham et al. . |
| 4,613,739 | 9/1986 | Richards . |
| 4,737,799 | 4/1988 | Kato . |
| 4,757,302 | 7/1988 | Hatakeyama et al. . |
| 4,761,891 | 8/1988 | Sugimura . |
| 4,768,155 | 8/1988 | Takishita et al. .................... 7/618 |
| 4,773,224 | 9/1988 | Sakamoto et al. . |
| 4,774,689 | 9/1988 | Morisawa . |
| 4,786,897 | 11/1988 | Takanashi et al. . |
| 4,786,916 | 11/1988 | Kato . |
| 4,819,189 | 4/1989 | Kikuchi et al. . |
| 4,831,548 | 5/1989 | Matoba et al. . |
| 4,847,696 | 7/1989 | Matsumoto et al. . |
| 4,855,550 | 8/1989 | Schultz, Jr. . |
| 4,901,179 | 2/1990 | Satomi et al. . |
| 4,920,337 | 4/1990 | Kuo . |
| 4,929,968 | 5/1990 | Ishikawa . |
| 4,942,514 | 7/1990 | Miyagaki et al. . |
| 4,965,610 | 10/1990 | Ishikawa . |
| 4,992,630 | 2/1991 | Mletzko . |
| 5,056,342 | 10/1991 | Prinz . |
| 5,068,802 | 11/1991 | Miyashita et al. . |
| 5,087,540 | 2/1992 | Murakami et al. . |
| 5,126,955 | 6/1992 | Tomoda . |
| 5,148,366 | 9/1992 | Buchanan et al. . |
| 5,151,974 | 9/1992 | Tani et al. . |
| 5,157,511 | 10/1992 | Kawai et al. . |

(List continued on next page.)

*Primary Examiner*—John E. Chapman
*Attorney, Agent, or Firm*—Brinks Hofer Gilson & Lione

[57] ABSTRACT

An ultrasound imaging system having an integrated touch-pad pointing device is provided. The touch-pad pointing device can be used to perform the functions currently performed by a trackball while overcoming the disadvantages commonly associated with trackballs. In addition to being integrated with the ultrasound imaging system, the touch-pad pointing device can also externally interface with the ultrasound imaging system, allowing the touch-pad pointing device to be easily added to existing ultrasound imaging systems that are not integrated with a touch-pad pointing device. Further, the touch-pad pointing device can be located on a remote user-interface device coupled with the ultrasound system to provide the further advantage of physically positioning the touch-pad pointing device closer to the user and away from the ultrasound machine.

3 Claims, 3 Drawing Sheets

U.S. PATENT DOCUMENTS

| | | |
|---|---|---|
| 5,185,515 | 2/1993 | Nishibe . |
| 5,201,034 | 4/1993 | Matsuura et al. . |
| 5,210,554 | 5/1993 | Cornsweet et al. . |
| 5,233,502 | 8/1993 | Beatty et al. . |
| 5,239,139 | 8/1993 | Zuta . |
| 5,293,326 | 3/1994 | Arima et al. ............................... 73/619 |
| 5,299,305 | 3/1994 | Oomae et al. . |
| 5,325,297 | 6/1994 | Bird et al. . |
| 5,335,180 | 8/1994 | Takahashi et al. . |
| 5,339,213 | 8/1994 | O'Callaghan . |
| 5,345,807 | 9/1994 | Butts et al. . |
| 5,355,355 | 10/1994 | Ohshima et al. . |
| 5,365,927 | 11/1994 | Roemer et al. . |
| 5,367,320 | 11/1994 | Taniguchi et al. . |
| 5,381,140 | 1/1995 | Kuroda et al. . |
| 5,382,777 | 1/1995 | Yuhara et al. . |
| 5,394,875 | 3/1995 | Lewis et al. . |
| 5,406,384 | 4/1995 | Sakuragi . |
| 5,414,420 | 5/1995 | Puckette et al. . |
| 5,415,840 | 5/1995 | Sano et al. . |
| 5,416,479 | 5/1995 | Jondrow et al. . |
| 5,428,355 | 6/1995 | Jondrow et al. . |
| 5,428,721 | 6/1995 | Sato et al. . |
| 5,430,553 | 7/1995 | Misono et al. . |
| 5,432,888 | 7/1995 | Iwamura et al. . |
| 5,436,792 | 7/1995 | Leman et al. . |
| 5,440,607 | 8/1995 | Nakaya . |
| 5,448,485 | 9/1995 | Ishibashi et al. . |
| 5,448,688 | 9/1995 | Hemingway . |
| 5,453,586 | 9/1995 | Stottmann . |
| 5,455,906 | 10/1995 | Usuda . |
| 5,458,126 | 10/1995 | Cline et al. . |
| 5,459,861 | 10/1995 | Oda . |
| 5,473,536 | 12/1995 | Wimmer . |
| 5,477,858 | 12/1995 | Norris et al. ............................... 73/626 |
| 5,490,039 | 2/1996 | Helms . |
| 5,506,023 | 4/1996 | Ohmori et al. . |
| 5,512,826 | 4/1996 | Hardy et al. . |
| 5,514,962 | 5/1996 | Cline et al. . |
| 5,526,814 | 6/1996 | Cline et al. . |
| 5,533,141 | 7/1996 | Futatsugi et al. . |
| 5,537,523 | 7/1996 | Harashima et al. . |
| 5,550,758 | 8/1996 | Corby, Jr. et al. . |
| 5,559,901 | 9/1996 | Lobregt . |
| 5,568,987 | 10/1996 | Franz . |
| 5,570,110 | 10/1996 | Shiga et al. . |
| 5,572,731 | 11/1996 | Morel et al. . |
| 5,584,293 | 12/1996 | Darrow et al. . |
| 5,584,294 | 12/1996 | Amemiya et al. ...................... 600/441 |
| 5,584,563 | 12/1996 | Stottmann . |
| 5,585,821 | 12/1996 | Ishikura et al. . |
| 5,590,658 | 1/1997 | Chiang et al. . |
| 5,592,945 | 1/1997 | Fiedler . |
| 5,602,508 | 2/1997 | Endou et al. . |
| 5,603,021 | 2/1997 | Spencer et al. . |
| 5,617,289 | 4/1997 | Abboud et al. . |
| 5,621,438 | 4/1997 | Kamimura et al. . |
| 5,623,406 | 4/1997 | Ichbiah . |
| 5,625,782 | 4/1997 | Soutome et al. . |
| 5,634,093 | 5/1997 | Ashida et al. . |
| 5,649,104 | 7/1997 | Carleton et al. . |
| 5,664,319 | 9/1997 | Abboud et al. . |
| 5,673,068 | 9/1997 | Jondrow et al. . |
| 5,673,156 | 9/1997 | Chen et al. . |
| 5,673,375 | 9/1997 | Horii . |
| 5,675,360 | 10/1997 | Takegoshi et al. . |
| 5,682,196 | 10/1997 | Freeman . |
| 5,684,259 | 11/1997 | Horii . |
| 5,687,136 | 11/1997 | Borenstein . |
| 5,694,142 | 12/1997 | Dumoulin et al. . |
| 5,696,916 | 12/1997 | Yamazaki et al. . |
| 5,699,494 | 12/1997 | Colbert et al. . |
| 5,706,195 | 1/1998 | Corby, Jr. et al. . |
| 5,706,517 | 1/1998 | Dickinson . |
| 5,715,451 | 2/1998 | Marlin . |
| 5,722,412 | 3/1998 | Pflugrath et al. . |
| 5,725,684 | 3/1998 | Inoue et al. . |
| 5,732,227 | 3/1998 | Kuzunuki et al. . |
| 5,755,576 | 5/1998 | Dunn et al. . |
| 5,755,986 | 5/1998 | Yamamoto et al. . |
| 5,757,616 | 5/1998 | May et al. . |
| 5,777,891 | 7/1998 | Pagano et al. ............................ 73/636 |
| 5,817,019 | 10/1998 | Kawashima ............................ 600/437 |
| 5,872,314 | 2/1999 | Clinton ................................. 73/620 |
| 5,919,138 | 7/1999 | Ustuner ................................. 600/437 |

# ULTRASOUND IMAGING SYSTEM WITH TOUCH-PAD POINTING DEVICE

BACKGROUND

There are several activities in an ultrasound examination that require a pointing device. These activities, which can include measuring, tracing, navigating, caliper placing, annotating, and menu selection, are typically performed using a trackball as a pointing device. There are, however, several disadvantages associated with using a trackball. First, because a trackball is not environmentally sealed, ultrasound coupling gel can collect within the internal mechanisms of the trackball and cause the trackball to malfunction, resulting in a costly service call. Second, trackballs are expensive and have a relatively high power consumption. Third, trackballs can be a source of repetitive stress injuries since a user is required to lift and reposition his hand to roll the pointer across the entire length of a displayed screen. Trackballs also occupy a large amount of space in the user-interface area on the ultrasound machine. Not only is this a limiting factor in size reduction of the user-interface area, but it is also a source of accidental activation of the pointing device.

There is, therefore, a need for an ultrasound imaging system with an improved pointing device that will overcome these disadvantages.

SUMMARY

The present invention is defined by the following claims, and nothing in this section should be taken as a limitation on those claims.

By way of introduction, the preferred embodiments described below include an ultrasound imaging system having an integrated touch-pad pointing device. The touch-pad pointing device can be used to perform the functions currently performed by a trackball while overcoming the disadvantages commonly associated with trackballs. In addition to being integrated with the ultrasound imaging system, the touch-pad pointing device can also externally interface with the ultrasound imaging system, allowing the touch-pad pointing device to be easily added to existing ultrasound imaging systems that do not have an integrated touch-pad pointing device. Further, the touch-pad pointing device can be located on a remote user-interface device coupled with the ultrasound system to provide the additional advantage of physically positioning the touch-pad pointing device closer to the user and away from the ultrasound machine.

The preferred embodiments will now be described with reference to the attached drawings.

DETAILED DESCRIPTION OF THE PRESENTLY PREFERRED EMBODIMENTS

Figure 1:
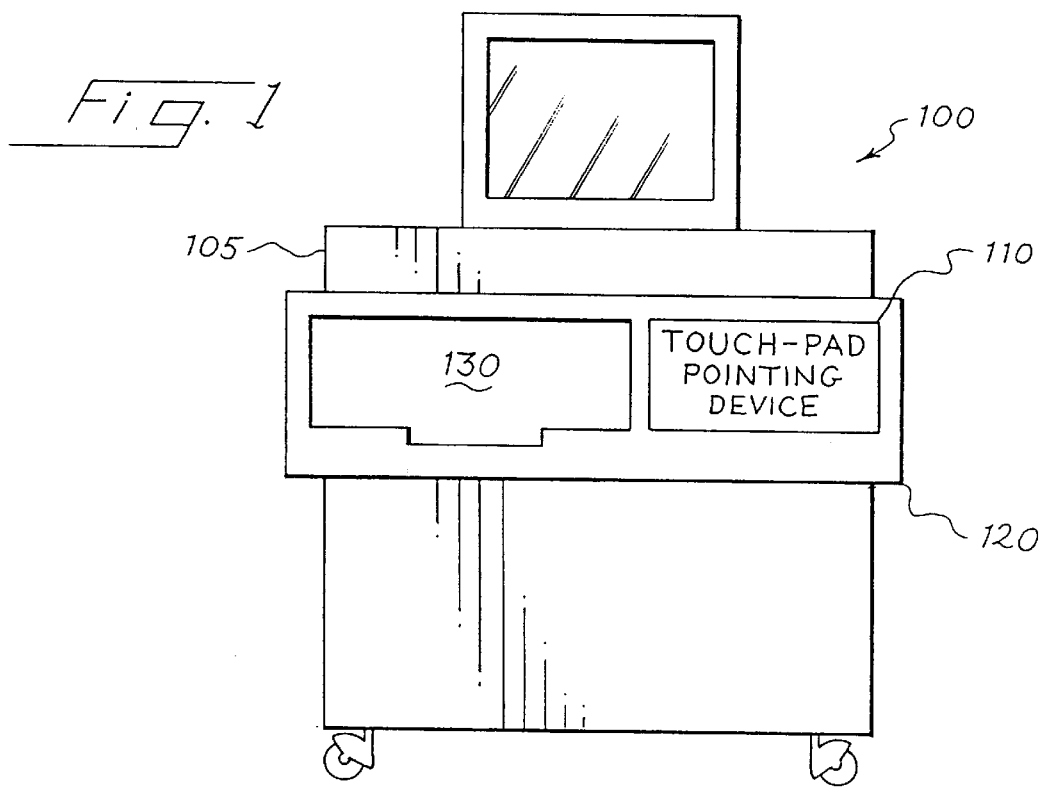
FIG. 1 is an illustration of an ultrasound imaging system of a first preferred embodiment.

Turning now to the drawings, FIG. 1 is an illustration of an ultrasound imaging system 100 that can be used to practice the presently preferred embodiments of this invention. As shown in FIG. 1, the ultrasound imaging system 100 comprises a housing 105 and a user-interface assembly 120. The user-interface assembly 120 comprises a touch-pad pointing device 110 and a user-interface input section 130. Although the touch-pad pointing device 110 is integrated with the housing 105 in this preferred embodiment, the touch-pad pointing device 110 and the housing 105 can be separate components, as described below. While the touch-pad pointing device 110 can be located at any acceptable location on the user-interface assembly 120, it is preferred that the touch-pad pointing device 110 be firmly supported from below to ensure proper function. To shield against electrostatic discharge and electromagnetic interference, it is preferred that the ground plate of the touch-pad pointing device 110 be contacted with metal and that the metal be attached to the chassis of the housing 105.

The user-interface input section 130 can comprise a standard QWERTY keyboard as well as ultrasound-specific function controls not found on standard QWERTY keyboards. For example, the user-interface input section 130 can comprise a gain control (which can be, but is not limited to, a rotatable knob) that changes the to intensity of the reflected ultrasound image. Another type of ultrasound-specific function control is a freeze control, which, when activated, freezes a displayed ultrasound image for further analysis. The freeze control can be, for example, a discrete key separate from other keys on a QWERTY keyboard, allowing a physician to immediately access the freeze control to capture an image of interest. The freeze control can take other forms in addition to a key.

Figure 2:
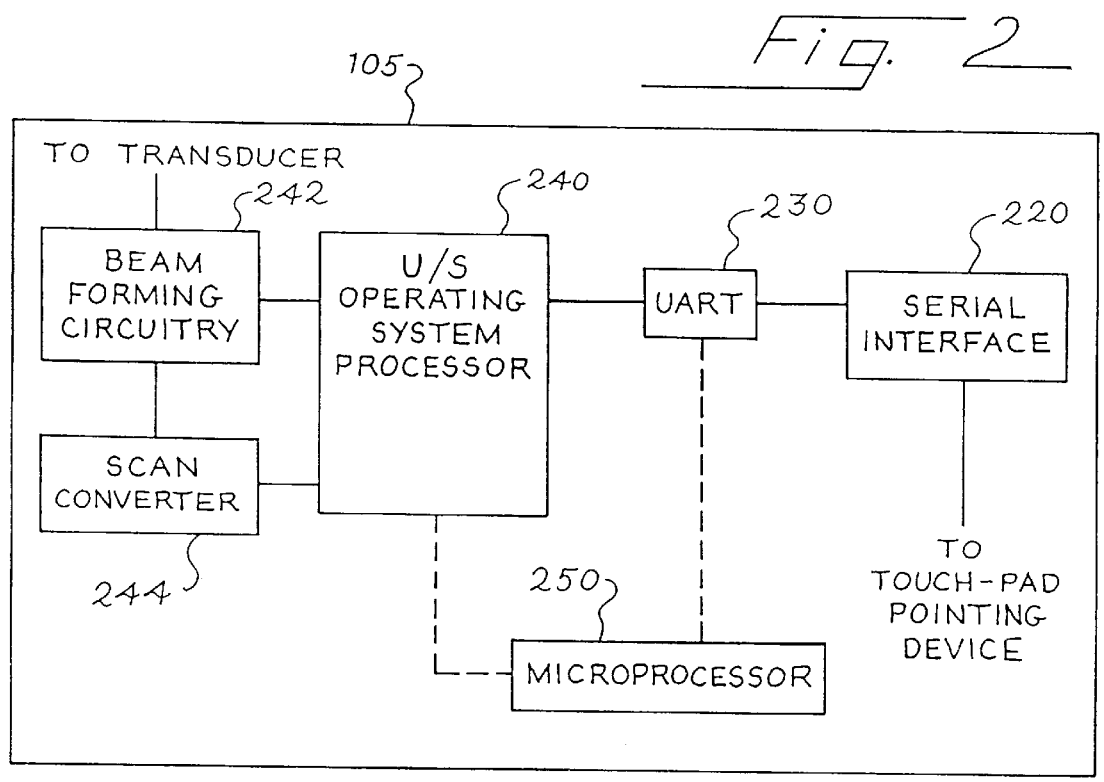
FIG. 2 is a block diagram of a preferred implementation of the ultrasound imaging system of FIG. 1.

FIG. 2 is a block diagram of a preferred implementation of the ultrasound imaging system 100 of FIG. 1. As shown in FIG. 2, the housing 105 carries beam forming circuitry 242 coupled with a transducer (not shown), a scan converter 244 coupled with the beam forming circuitry 242, and an ultrasound operating system processor 240, which controls the operation of the beam forming circuitry 242 and the scan converter 244. As used herein, the term "coupled with" means directly coupled with or indirectly coupled with through one or more components. With these components and the housing, the ultrasound imaging system weighs more than about 50 pounds. As is well known by those in the art, the beam forming circuitry 242 applies a voltage to the transducer to cause it to vibrate and emit ultrasonic energy and also measures the voltages created by the transducer when reflected ultrasonic energy impinge on the transducer. The scan converter 244 processes the amplified, sensed voltages to create an image associated with the reflected signals.

In this preferred embodiment, the touch-pad pointing device is coupled with the ultrasound operating system processor 240 via a serial interface 220 and a Universal Asynchronous Receiver/Transmitter ("UART") serial-to-parallel converter 230. It is preferred that the serial interface 220 be a standard TTL voltage-level serial interface. The UART 230 can communicate directly with an ultrasound operating system processor 240 (as shown by the solid connecting line in FIG. 2) or indirectly, via its bi-directional parallel interface, with a function-specific microprocessor 250 (as shown by the dashed connecting lines in FIG. 2). The touch-pad pointing device can receive power to operate via the ultrasound imaging system's power source as part of the integration design.

Figure 3:
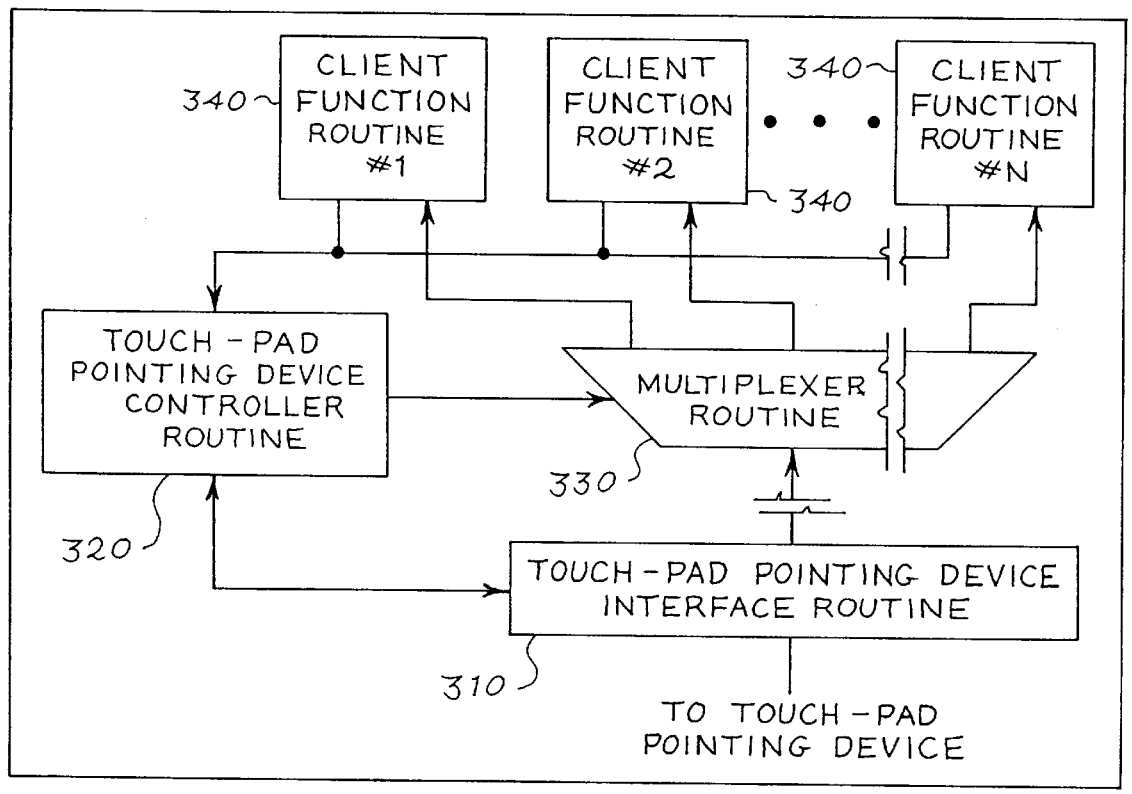
FIG. 3 is a block diagram of a software architecture of a preferred embodiment.

FIG. 3 is a block diagram of a preferred software architecture implemented in the ultrasound imaging system 100. As described below, all or part of the preferred software architecture can be implemented in the ultrasound operating system processor 240 or in the microprocessor 250. As shown in FIG. 3, the preferred software architecture comprises a pointing device interface routine 310, a pointing device controller routine 320, and a multiplexer routine 330. The pointing device controller routine 320 and the multiplexer routine 330 are both coupled with a plurality of ultrasound client function routines 340, which can enable, for example, caliper movements, manipulation of the position and size of the color box area of interest, text editor pointing, and list scrolling.

In operation, the pointing device interface routine 310 converts signals from the touch-pad pointing device into a form usable by the ultrasound imaging system, and the pointing device controller routine 320 directs the converted signals to the appropriate client function routine 340. Upon receiving instructions from the pointing device controller routine 320, the pointing device interface routine 310 transmits commands to and receives configuration data from the touch-pad pointing device to detect position information. Because a client function routine 340 may not be able to use absolute position information, the pointing device interface routine 310 can convert the position data to clipped and scaled logical position data, emulating the type of position information that the client function routine 340 expects to receive from a trackball. The pointing device controller routine 320 then directs the logical position data via the multiplexer routine 330 to one of the client function routines 340. A specific client function routine 340 can receive the scaled logical position data on demand or as the position data changes. If only one ultrasound client function routine is used, the pointing device interface routine 3 10 can be coupled to the ultrasound client function routine without the use of the pointing device controller routine 320 or the multiplexer routine 330.

The touch-pad pointing device can be used to perform the functions currently performed by a trackball while overcoming the disadvantages commonly associated with trackballs. First, touch-pad pointing devices are environmentally sealed thereby eliminating malfunctions and costly service calls that are common with trackballs. Reliability is further increased with touch-pad pointing devices since there are no moving parts. Second, touch-pad pointing devices have a relatively low power consumption when compared to trackballs and are about five-times less expensive than trackballs. Because of its significantly lower cost, a defective touch-pad pointing device can replaced instead of repaired, making it more disposable than a trackball.

Third, compared to trackballs, touch-pad pointing devices require less space on the user-interface area, thereby promoting user-interface size reduction. Additionally, accidental activation is less likely with touch-pad pointing devices than with trackballs since the thickness envelope of a touch-pad pointing device (typically less than about 0.5 inches) is less than the protrusion height of a trackball (typically about one inch). Further, virtually any contact with a trackball will cause it to roll and activate, while a touch-pad pointing device will typically only activate with the touch of a finger on the flat touch-pad area. Fourth, because touch-pad pointing devices do not require much pressure to operate and because touch-pad pointing devices perform tap and double-tap selection without leaving the pad's surface or using separate buttons, repetitive stress injuries can be reduced.

Finally, in contrast to a trackball, which provides data that has to be interpreted to determine direction and magnitude of change, the touch-pad pointing device provides encoded, absolute position data. Since the data from a touch-pad pointing device does not need to be interpreted, the touch-pad pointing device requires a less-complicated software interface. Also, in contrast to a trackball, the touch-pad pointing device can be configured to add a new dimension to the position data. The trackball position information is only a relative change to a prior logical position value. The touch-pad pointing device, however, senses both the finger's position and its contact area, which is a measure of the applied pressure. Therefore, the touch-pad can send absolute X, Y, and Z (pressure) information that can produce low fatigue pointing action via pressure-activated panning and scrolling, for example.

Figure 4:
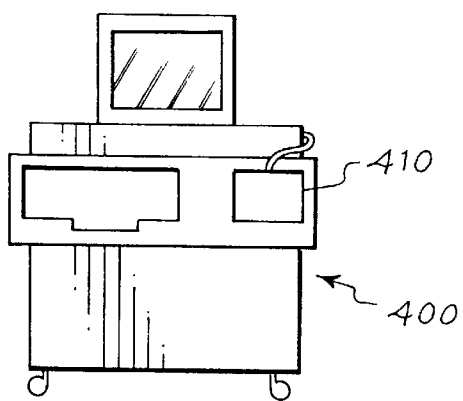
FIG. 4 is an illustration of an ultrasound imaging system of another preferred embodiment in which a touch-pad pointing device interfaces with the ultrasound imaging system as an external device.

As discussed above, although FIG. 1 shows a touch-pad pointing device integrated with the ultrasound imaging system housing, the touch-pad pointing device can also externally interface with the ultrasound imaging system. FIG. 4 shows an ultrasound imaging system 400 with an externally-attached touch-pad pointing device 410. In addition to the advantages described above, the embodiment shown in FIG. 4 provides the advantage of allowing a touch-pad pointing device to be easily added to an existing ultrasound imaging system that does not have an integrated touch-pad pointing device.

Figure 5:
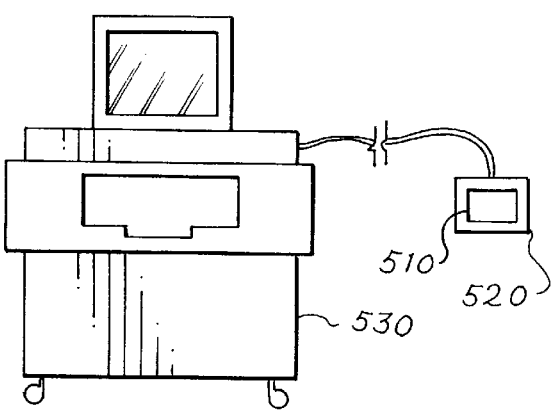
FIG. 5 is an illustration of an ultrasound imaging system of another preferred embodiment in which a remote user-interface device carries a touch-pad pointing device.

FIG. 5 shows another alternative in which a user-interface device 520 remotely located from the ultrasound imaging system housing 530 carries a touch-pad pointing device 510. In addition to the advantages described above, having the touch-pad pointing device 510 be located on a remote user-interface device 520, such as a pendant controller, provides the further advantage of physically positioning the touch-pad pointing device closer to the user and away from the ultrasound machine. Additional user controls can also be placed on the remote user-interface device 520.

Figure 6:
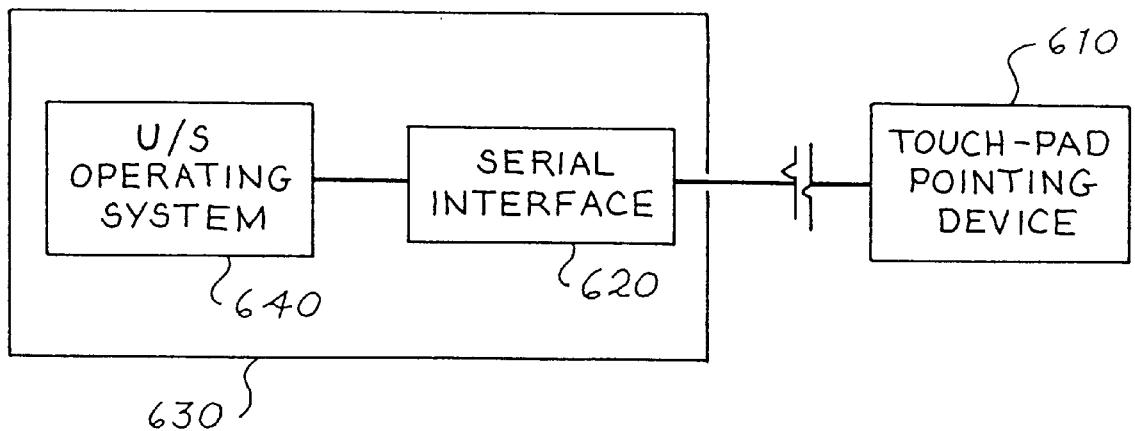
FIG. 6 is a block diagram of a preferred implementation of the ultrasound imaging systems of FIGS. 5 and 6.

FIG. 6 is a block diagram of a preferred implementation of the ultrasound imaging systems of FIGS. 5 and 6. As shown in FIG. 6, the touch-pad pointing device 610 is coupled with a serial interface 620 on a user-accessible I/O panel on the ultrasound imaging system housing 630. It is preferred that the serial interface 620 be a standard RS-232 serial interface port. The serial interface 620 is coupled with the ultrasound operating system processor 640, and the touch-pad pointing device's 610 configuration commands and position information can be transferred to and from the ultrasound operating system processor 640 using standard ASCII codes. The touch-pad pointing device 610 can receive power to operate via a RS-232 serial port, thus eliminating an external power supply.

As shown in FIGS. 4–6, the touch-pad pointing device can be physically coupled with the ultrasound imaging system using, for example, cabling or fiber optical coupling. Alternatively, the touch-pad pointing device can be coupled via a wireless connection using, for example, infrared, radio-frequency or audible signals.

For simplicity, the term "ultrasound operating system processor" is used in the specification and claims to broadly refer to hardware and/or software (now in existence or later developed) that can be used to control the operation of an ultrasound imaging system. The widest variety of devices can be used to implement the ultrasound operating system processor. It is preferred that the routines described above be implemented with software. A computer-usable medium having computer readable program code embodied therein can be used to perform the functions described above. As discussed below, the code performing the functions described above can be distributed among more than one medium. It is important to note that any appropriate software language and any appropriate hardware, analog or digital, can be used. Also, the functions associated with the routines can also be implemented exclusively with hardware.

To illustrate the presently preferred embodiments, the above figures show devices and routines as separate elements. It is important to note, however, that these separate elements can be combined. Further, the functionality associated with each element can be combined with or distributed to other elements. For example, the functionality shown in FIG. 3 can be implemented exclusively in the ultrasound operating system processor 240, exclusively in the microprocessor 250, or implemented in part in the ultrasound operating system processor 240 and in part in the microprocessor 250. Also, some of the elements described above may not be needed in all embodiments.

Figure 7:
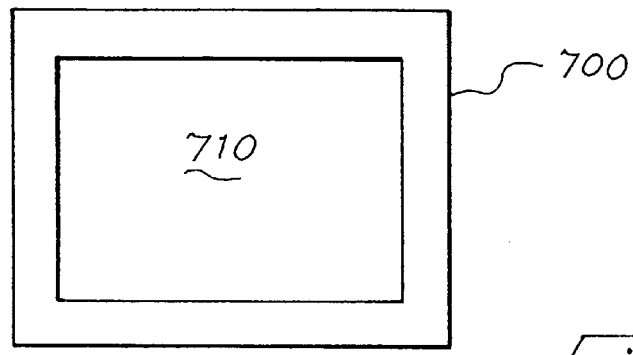
FIG. 7 is an illustration of a touch-pad pointing device of a preferred embodiment, in which a bezel is placed over the touch-pad pointing device.
Figure 8:
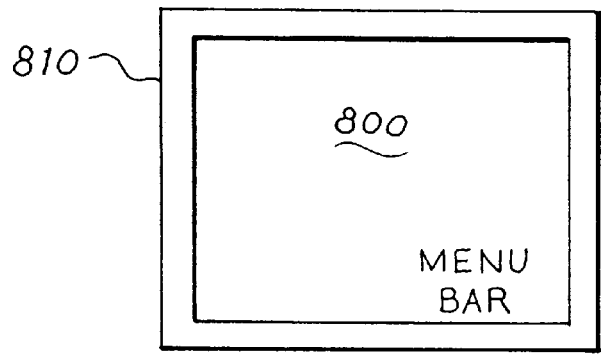
FIG. 8 is an illustration of a touch-pad pointing device of a preferred embodiment, in which an overlay is placed over the touch-pad pointing device.

With any of the above embodiments, a bezel 700 can be placed over the touch-pad pointing device 710 to secure the device and cover any unfinished edges (see FIG. 7). The bezel can also be shaped (e.g., round, square, or rectangular) for optimized functionality. For example, a round-shaped bezel can be used as a mask to more accurately resemble a circular area of a trackball. As another example, if the location selected on the touch-pad pointing device moves a pointer to a corresponding location on the display screen, the bezel can be shaped to have an aspect ratio corresponding to the aspect ratio of the display screen. Additionally, if specific areas of the touch-pad pointing device are associated with particular functions (e.g., the lower right-hand corner activates a menu bar), an embossed or removable text or graphics overlay 800 can be placed over the touch-pad pointing device 810 to aid a user to locate a desired area (see FIG. 8).

The foregoing detailed description has described only a few of the many forms that this invention can take. Of course, many changes and modifications are possible to the preferred embodiments described above. For this reason it is intended that this detailed description be regarded as an illustration and not as a limitation of the invention. It is only the following claims, including all equivalents, that are intended to define the scope of this invention.

What is claimed is:

1. A medical diagnostic ultrasound imaging system comprising:

beam forming circuitry;

a scan converter coupled with the beam forming circuitry;

an ultrasound operating system processor coupled with the beam forming circuitry;

a display coupled with the ultrasound operating system processor and operative to display a medical diagnostic ultrasound image;

a housing carrying the beam forming circuitry, scan converter, and ultrasound operating system processor, and a touch-pad pointing device coupled with the ultrasound operating system processor, the touch-pad pointing device being operative to position a pointer on the medical diagnostic ultrasound image displayed on the display;

wherein the touch-pad pointing device comprises a plurality of corners and wherein the invention further comprises a bezel adjacent the touch-pad pointing device, the bezel being shaped to cover at least one corner of said plurality of corners.

2. A medical diagnostic ultrasound imaging system comprising:

beam forming circuitry;

a scan converter coupled with the beam forming circuitry;

an ultrasound operating system processor coupled with the beam forming circuitry;

a display coupled with the ultrasound operating system processor and operative to display a medical diagnostic ultrasound image;

a housing carrying the beam forming circuitry, scan converter, and ultrasound operating system processor; and a touch-pad pointing device coupled with the ultrasound operating system processor, the touch-pad pointing device being operative to position a pointer on the medical diagnostic ultrasound image displayed on the display;

wherein the ultrasound imaging system is associated with a display screen characterized by an aspect ratio and wherein the invention further comprises a bezel adjacent the touch-pad pointing device, the bezel being shaped to have an aspect ratio corresponding to the aspect ratio of the display screen.

3. A medical diagnostic ultrasound imaging system comprising:

beam forming circuitry;

a scan converter coupled with the beam forming circuitry;

an ultrasound operating system processor coupled with the beam forming circuitry;

a display coupled with the ultrasound operating system processor and operative to display a medical diagnostic ultrasound image;

a housing carrying the beam forming circuitry, scan converter, and ultrasound operating system processor;

a touch-pad pointing device coupled with the ultrasound operating system processor, the touch-pad pointing device being operative to position a pointer on the medical diagnostic ultrasound image displayed on the display; and an overlay adapted to at least partially cover the touch-pad pointing device.

* * * * *